United States Patent [19]

Huntley et al.

[11] Patent Number: 5,683,444
[45] Date of Patent: Nov. 4, 1997

[54] COMPOSITE ELECTRODE

[76] Inventors: Steve Huntley, 271 Baker St. West, St. Paul, Minn. 55107; Duane J. Zytkovicz, 28454 U.S. Hwy. 169, Onamia, Minn. 56359; Manfred Geiger, Rotwandstrauss 12, 81539 Munchen, Germany

[21] Appl. No.: 570,306

[22] Filed: Dec. 11, 1995

[51] Int. Cl.⁶ ................................................ A61N 1/05
[52] U.S. Cl. ................................................ 607/122
[58] Field of Search ........................... 607/116, 119, 607/122–132; 128/642

[56] References Cited

U.S. PATENT DOCUMENTS

| | | | |
|---|---|---|---|
| 5,005,587 | 4/1991 | Scott | 607/122 |
| 5,014,721 | 5/1991 | Hirchberg | 607/122 |
| 5,143,089 | 9/1992 | Alt . | |
| 5,336,254 | 8/1994 | Brennen et al. | 607/128 |
| 5,411,527 | 5/1995 | Alt | 128/642 X |
| 5,433,730 | 7/1995 | Alt | 607/123 X |

OTHER PUBLICATIONS

Alt et al. *Improved Defibrillation Threshold With A New Epicardial Carbon Electrode Compared With A Standard Epicardial Titanium Patch*, pp. 445–450, Circulation, vol. 91, No.2, Jan. 15, 1995.

Alt, et al. *Endocardial Carbon–Braid Electrodes*, pp. 1627–1633, Circulation, vol. 92, No. 6, Sep. 15, 1995.

*Primary Examiner*—Jeffrey R. Jastrzab
*Attorney, Agent, or Firm*—Joel D. Skinner, Jr.

[57] ABSTRACT

An implantable assembly for defibrillation and monitoring and/or regulating the beat of a heart. The defibrillation electrode is flexible and preferably made of braided carbon fiber and conductive metallic wire. It provides a low polarization, low capacitance and low impedance electrical interface with body fluid and/or excitable tissue. The conductivity of the defibrillation electrode is increased over electrodes made only of carbon fiber by the presence of the conductive metallic wire in the preferred embodiment, or by a thin exterior coating of titanium and silver in another embodiment. This electrode delivers energy more efficiently to body tissue than conventional defibrillation electrodes, resulting in lower energy needed to achieve defibrillation, which allows batteries powering the defibrillator to last longer. The fibers together provide an effective surface area for the electrical interface which is considerably larger than the apparent actual surface area of the electrode as determined from the linear dimensions of the electrode. This lows the electrode to be smaller than conventional defibrillation electrodes. The preferred configuration of the defibrillation electrode is tubular, which can be used with at least one additional device, such as a second electrode for pacing or sensing the heartbeat, to be mounted on the distal end of the defibrillator electrode. Lead(s) connected to the additional device(s) pass through the defibrillator electrode and run inside the lead connected to the defibrillator electrode.

18 Claims, 4 Drawing Sheets

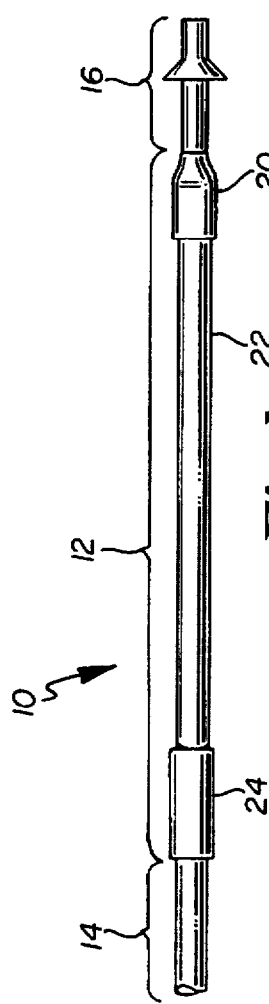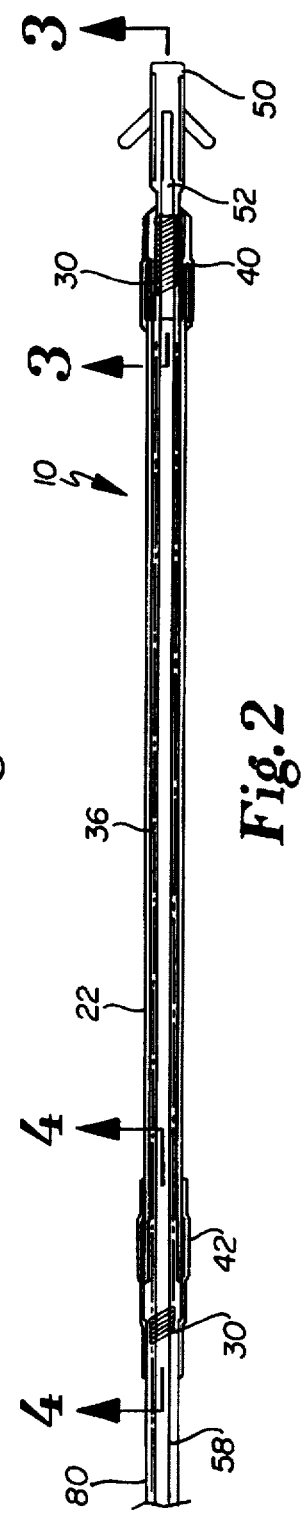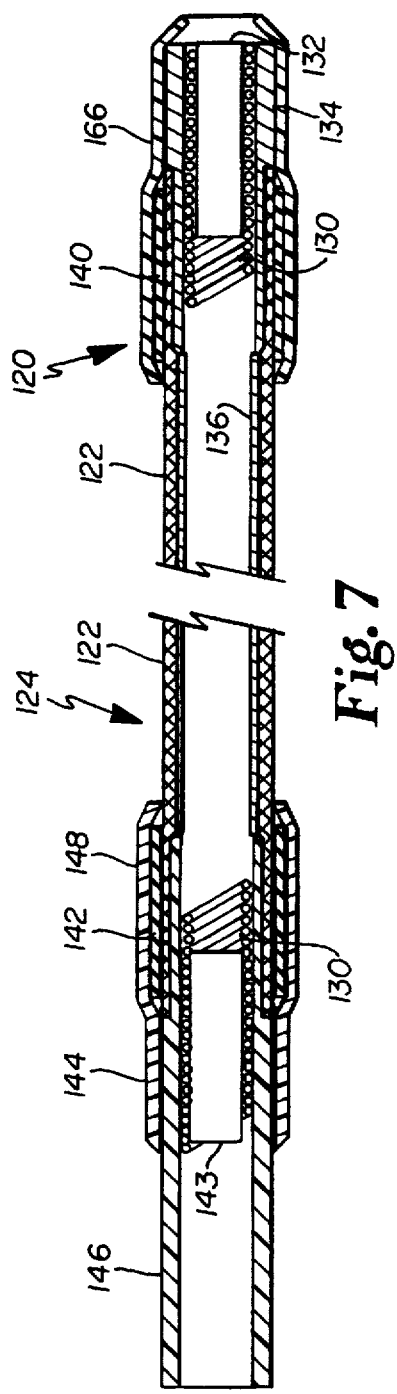

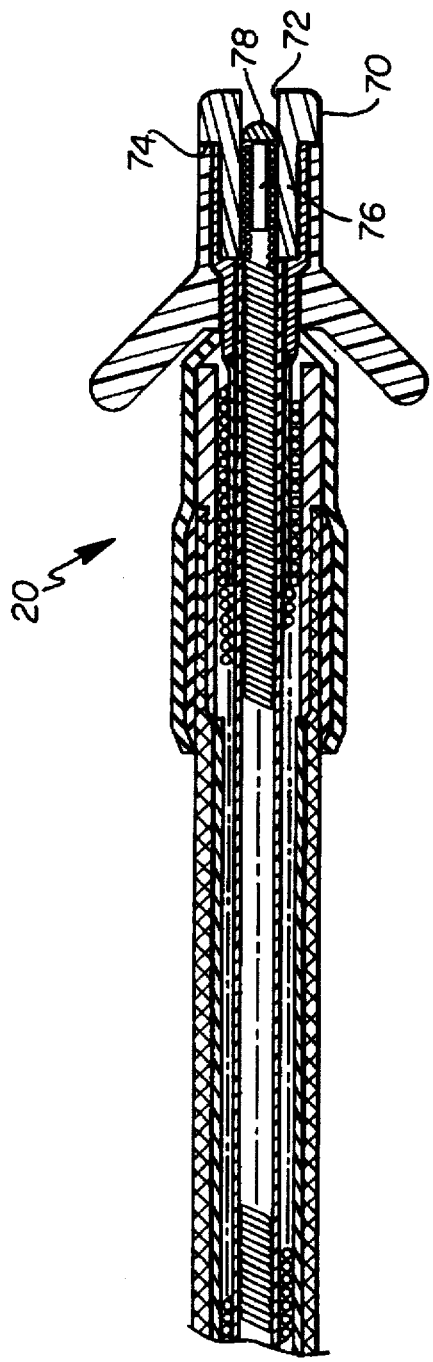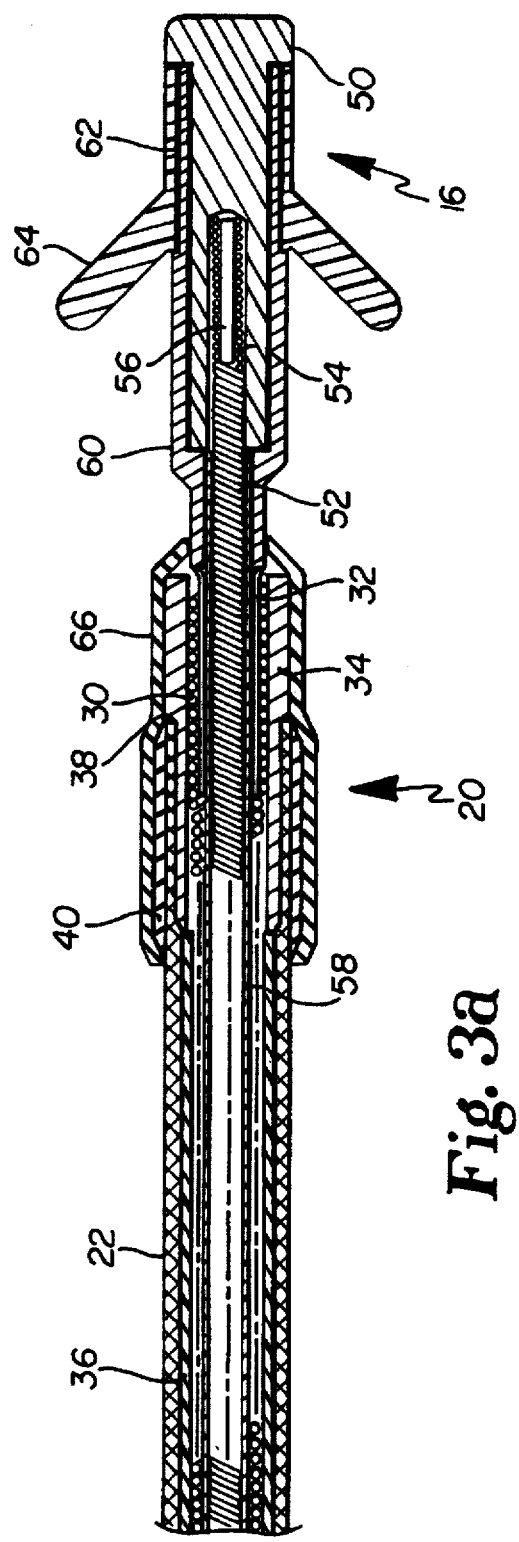
Fig. 3b
Fig. 3a

COMPOSITE ELECTRODE

BACKGROUND OF THE INVENTION

1. Field of the Invention

The present invention relates, generally to electro-medical devices. More particularly, the invention relates to improved implantable electrodes for interfacing with human body tissue and resulting improved electrical therapeutic systems. The invention has particular utility in implantable cardioverter-defibrillators. However, the invention also may be found to have utility in other applications such as neural stimulation or stimulation of non-cardiac muscle tissue.

2. Background Information

The development of defibrillators over the past thirty years was thoroughly described in U.S. Pat. No. 5,143,089 issued to Eckhard Alt. Alt's electrode, made from a bundle of synthetic fibers, began to address the need for electrodes interfacing with body tissue which have large surface area, low polarization, and little intrinsic stiffness with the capacity for good communication and high current over long life.

Carbon is among the suitable materials for the fibers disclosed in the Alt '089 patent. Carbon fiber is well suited for processing into interlaced forms, and has been the subject of further development. The Alt '089 patent suggested a woven flat patch or a tubular woven structure made from the fibers.

Dr. Alt continued development and testing of fiber defibrillator electrodes. In U.S. Pat. No. 5,411,527, Alt disclosed the use of tiny metallic fibers having a smooth uniform coating of carbon on them. In U.S. Pat. No. 5,433,730, Alt disclosed a conductive pouch electrode where the pouch has "an effective electrical surface area considerably larger than its geometric surface area."

Electrodes must have some way of being connected to a power source. This is usually done by connecting one end of a metal lead to the electrode and the other end to the power source. The '089 patent does not discuss how the fiber electrode is connected to the lead attached to it, and it shows a lead being connected only at one end of the fiber electrode. The '089 patent disclosed electrodes made completely of carbon fiber, and some of the configurations had the fiber bundles interwoven. Such a structure requires electricity to be conducted through the connection between the lead and the electrode and to be conducted throughout the electrode by the carbon fiber filaments themselves. While carbon fiber does conduct electricity, it is not as good a conductor as metal. Consequently, there can be some significant voltage gradient down the length of the electrode. A voltage that is below the minimum threshold needed to induce defibrillation is ineffective. If a voltage gradient along the electrode causes a section of the electrode to have a voltage below this minimum, that section of the electrode is ineffective.

It is an object of the present invention to provide a carbon fiber and metallic conductor electrode which has higher conductivity than electrodes made only of carbon fiber.

It is a further object of this invention to provide a method of connecting a carbon fiber electrode to a metallic lead that maintains the structural integrity of the carbon fiber electrode and provides redundant electrical paths between the electrode and the lead.

It is a further object of this invention to provide an electrode which is more efficient in transferring energy to living tissue, particularly a heart.

It is a further object of this invention to provide a high efficiency electrode which is flexible and three dimensional.

It is a further object of this invention to provide an electrode which requires lower energy to accomplish defibrillation of a heart.

It is a further object of this invention to provide an electrode which allows energy sources used with it to have longer useful lives.

It is a further object of this invention to provide an electrode which allows energy sources used with it to be smaller.

It is a further object of this invention to provide an electrode for defibrillation of a heart which can be used in combination with many other electrodes.

SUMMARY OF THE INVENTION

The present invention provides an improved electrode structure and attached lead for defibrillation. The improved structure provides increased conductivity over carbon fiber electrodes and eliminates any significant voltage gradient along the electrode by 1) interspersing highly conductive metal wire, preferably made of platinum-iridium, among the carbon fiber bundles, or coating outer fibers with conductive metal and 2) connecting the fiber electrode at both ends to an electrical lead in a manner that maintains the structural integrity of the fiber electrode and provides redundant electrical paths between the electrode and lead.

The fiber electrode configuration provides a low polarization, low capacitance, low resistance, and low impedance electrical interface with body fluid and/or excitable tissue in contact with or in the immediate vicinity of the electrode. The electrode has a distal end and a proximal end, is flexible, and, in the preferred embodiment, is comprised of a multiplicity of uninsulated current-conducting fibers and wires. Those fibers and wire are braided to maintain the electrode's shape. The fibers together provide an effective surface area for the electrical interface which is considerably larger than the apparent actual surface area of the electrode as determined from the linear dimensions of said electrode. In an alternate embodiment, there is no wire braided with the fibers, rather the fibers exposed on the surface of the electrode are coated with a thin layer of titanium followed by a thin layer of silver.

The fiber electrode is attached to a conductive lead at both ends of the electrode by swaging a compression ring of platinum-iridium over the ends of the electrode. That makes a good electrical and mechanical connection between the electrode and the lead and the platinum-iridium is soft enough to not damage the carbon fiber during the swaging process.

In one embodiment of the invention, the electrode and attached lead are tubular to facilitate its use for heart defibrillation in combination with a different type second electrode and attached lead used for pacing or sensing the heartbeat. The second electrode is mounted distally with respect to the tubular defibrillation electrode. The lead attached to the second electrode runs coaxially inside the tubular defibrillation electrode and inside of the first lead for a substantial length of the first lead. The two coaxial leads are terminated in a manner well known in the industry to connect to an energy source not a part of this invention.

In another embodiment of the present invention, a tubular braided fiber electrode has a distal fitting attached to one end of it and a proximal fitting attached to the other end. The proximal fitting can be configured in any manner to facilitate connection to an energy source or another lead not a part of this invention. Both fittings may be tubular to allow additional leads for additional electrodes to pass through the bore of the braided fiber electrode.

The preferred tubular construction of the electrode of the present invention allows ancillary structures than electrodes to be used in conjunction with the electrode. Such structures include drug dispensers and fiber optics.

The features, benefits and objects of this invention will become clear to those skilled in the art by reference to the following description, claims and drawings.

BRIEF DESCRIPTION OF THE DRAWINGS

FIG. 1 is an overall view of the preferred embodiment of the composite electrode and lead of the present invention as used in conjunction with a pace/sense electrode.

FIG. 2 is a view partially in cross section of the preferred embodiment shown in FIG. 1.

FIG. 3A is a cross sectional view of the distal end of the preferred embodiment shown in FIG. 1.

FIG. 3B is a cross sectional view of an alternate embodiment of the distal end shown in FIG. 3A.

FIG. 7 is a cross sectional view of an alternate embodiment of the present invention.

DETAILED DESCRIPTION

1. General Principles

A) Improved Conductivity

Figure 4:
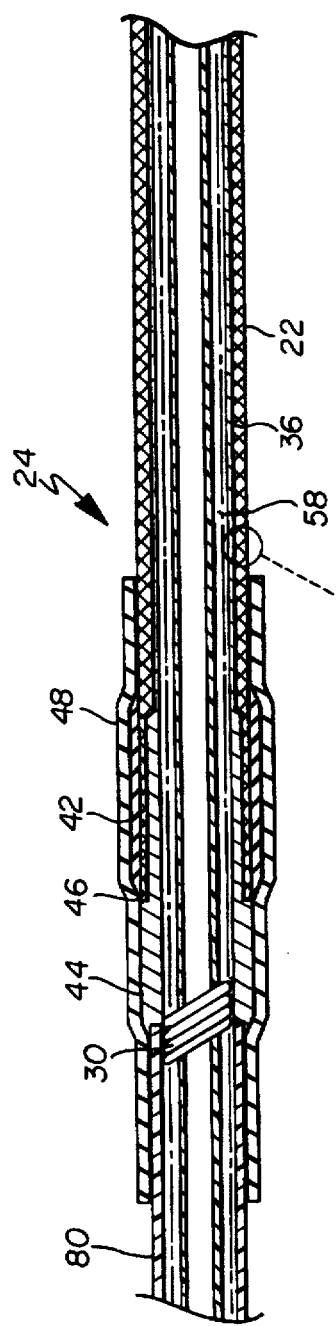
FIG. 4 is a cross sectional view of the proximal end of the preferred embodiment shown in FIG. 1.

One aspect of the invention is the improved conductivity of the carbon fiber electrode. Pyrolized carbon and platinum-iridium have been used for pacemaker electrodes which operate in the 2.5 to 5 volt range. Both materials are low-polarizing, which reduces energy consumption. Carbon in fiber form provides added advantages of flexibility, strength, and most importantly, a very large surface area. Each filament of carbon fiber can have a diameter of about 10 microns. A bundle of filaments, called a tow, having about 1000 filaments, has a diameter of about 0.2 mm and a total surface area of about 3 square centimeters per centimeter of tow length. This is particularly advantageous for defibrillation where several hundred volts are applied. To apply such voltage to cardiac tissue without inflicting local burns requires electrodes with surface areas of 50 to 100 square centimeters. With tows of carbon fiber, only a few centimeters of material are needed to provide the required surface area. This means a carbon fiber electrode can be much smaller than conventional electrodes, making implantation easier. Furthermore, the high flexibility of carbon fiber allows maximum myocardial contact upon movement of the heart, and minimum restriction of the myocardial function.

However, carbon fiber is not a very good conductor. Consequently, an electrode made only of carbon fiber may show a voltage gradient which could be detrimental to the functioning of the electrode. To improve the conductivity over carbon fiber electrodes, the present invention preferably intersperses highly conductive wire among the carbon fiber tows during the process of forming the electrode. The wire used in the preferred embodiment was 90/10 platinum-iridium.

When the carbon fiber bundles and wire are woven or braided into a structure, the resulting structure has multiple redundant paths of high conductivity formed by the intersecting wires. There is essentially a "mesh" of highly conductive material (wire) with lower conductive material (carbon fiber) in the spaces of the mesh. The finer the mesh, the lower the voltage gradient in the carbon fiber. The result is an electrode with the advantages of the fiber electrode made only from carbon fiber, but with a higher conductivity, and thus a lower voltage gradient.

In a test performed to verify the higher conductivity, a multimeter measured the resistance of 1) platinum iridium wire (9/49 style), 2) a braided tube made of carbon fiber (16 tows of Toray T-300 1K fiber), and 3) a braided tube made from 12 tows of Toray T-300 1K carbon fiber and 4 strands of 9/49 platinum iridium wire. The resistance of the platinum iridium wire itself was 1.1 ohms/ft. The resistance of the tube made from only carbon fiber was 11.2 ohms/ft. The resistance of the tube made from carbon fiber and platinum iridium wire was 4.0 ohms/ft.

The high surface area of carbon fiber and the increased conductivity from the addition of the wire result in an electrode that requires lower voltages and energies to achieve defibrillation. The present invention preferably uses a combination of platinum-iridium wire and carbon fiber tows (PIC) braided together in a tubular form. It is well suited for use where a combination endocardial and epicardial electrodes are used for defibrillation.

The present invention was tested in the endocardial configuration and position. The PIC electrode was one of three endocardial electrodes tested in combination with the two epicardial electrodes on dogs' hearts to determine the most effective combination for defibrillation. The epicardial electrode attached to the outside of the heart was either a conventional titanium patch or a braided tubular carbon fiber electrode attached in a U shape describing the outer bounds of the patch. The endocardial electrode was placed at a location inside the heart.

The results of the testing showed that of the two epicardial electrodes, the braided carbon fiber electrode reduced the energy required to achieve defibrillation 39 to 56 percent, and lowered the voltage required 24 to 35 percent over the titanium patch. The greatest reduction was achieved with the PIC electrode for the endocardial electrode. Of the three endocardial electrodes, the PIC electrode also produced the lowest defibrillation energies for both the titanium patch and the braided carbon fiber electrode.

B) Connection to Lead

Another aspect of the present invention is way the metal lead is attached to the fiber electrode. A swage joint is made preferably at both ends of the fiber electrode so the fiber electrode is attached to the lead at two places. That provides redundant electrical paths between the electrode and the lead and further reduces the voltage gradient along the electrode. The resultant low capacitance electrode has low polarization and better coupling to provide low energy loss at the electrode-lead connection.

The swaging operation compresses a metal swage ring onto the ends of the braided fiber tube. A metal internal tube segment supports the braided fiber during this operation. The swage ring material must be very soft to flow around the carbon fiber and not fracture it. If the swage ring material is not soft enough, locally high compression forces can damage the fiber. This is different from swaging metal braided tubes where the metal braid will deform along with the swage ring to make a unitized structure. With carbon fiber braided tubes, if too high a compressive load is applied, the fiber will fracture resulting in a poor electrical connection.

If the fracturing is severe enough, the swaged end may break away from the rest of the structure.

The present invention preferably uses a 90/10 platinum iridium material for the swage ring. That material is soft enough to make a good swage joint without significantly damaging the fiber. Pure annealed platinum, which is even softer could also be used, or any conductive, malleable, non-reactive metal such as gold or rhodium alloys.

2. Preferred Embodiments

Referring to the drawings, where like reference numerals designate like or similar elements throughout, a preferred embodiment of the invention is illustrated in FIGS. 1 through 4.

Referring to FIG. 1, a composite electrode assembly 12 of the present invention is used in conjunction with a pace/sense electrode assembly 16 and transmission section 14 to form part of an implantable assembly 10. The electrode assemblies 12 and 16 are positioned near the tissue to be stimulated and ideally in contact with the tissue to be sensed. Transmission section 14, which can be any length, carries leads (not shown) connected to electrode assemblies 12 and 16. Terminations of the leads are made in any manner well known in the industry to connect to an energy source, and are not a part of this invention. The composite electrode assembly 12, has a distal end 20, and a proximal end 24 with approximately 5 cm of exposed conductor 22 between them. The conductor 22 constitutes the defibrillation electrode and, in the preferred embodiment, is a structure made of carbon fiber and conductive metal wire braided together.

Referring to FIG. 2, leads 30 and 52 are coiled wire which run essentially the entire length of the implantable assembly 10. The coiled configuration of these leads provides great longitudinal flexibility making it easy for surgeons to manipulate the implantable assembly 10. It also provides great radial stiffness to resist crushing when handled by people and surgical instruments. Lead 52 runs coaxially inside lead 30, and the two are electrically and mechanically separated by insulating tubing 58, such as polyurethane. One end of lead 52 is mechanically and electrically fastened to electrode 50, which is a pace/sense type electrode. One end of lead 30 is mechanically and electrically fastened to conductor 22 at both ends of conductor 22 by distal compression ring 40 and proximal compression ring 42. A piece of insulating tubing 36 is also optionally installed over lead 30 at the location of the braided conductor 22 to make it easier to slip braided conductor 22 over lead 30.

A length of insulating tubing 80 sheaths lead 30 in transmission section 14. Leads 30 and 52 can be any length and can be terminated in many configurations to meet requirements of mating parts.

The implantable assembly 10 provides a compact package of a most efficient defibrillator electrode assembly 12 and a pace/sense electrode assembly 16. The conductor 22 of defibrillator electrode assembly 12 provides a high voltage shock to a fibrillation heart to restore normal rhythm. The pace/sense electrode 50 of the pace sense electrode assembly 16 senses the natural electrical signal produced by a beating heart and/or provides a low voltage stimulation to maintain a desired pace of the heartbeat. A device of this configuration can easily be placed in the desired location to provide part of the electrical stimulation and sensing needed to control a malfunctioning heart. At least one other electrode is needed to complete the defibrillation circuit. That could be provided by another device of this configuration attached at a different location, or by some other electrode configuration.

The method of construction of the composite electrode assembly 12 of the preferred embodiment of the device is shown in FIGS. 2, 3A, and 4. Referring to FIG. 3A, the distal end 20 is assembled as follows. An appropriate length of coil lead 30 is selected. In the preferred embodiment it was Quadrifilar MP35N/AG 0.054 in. dia. Distal crimp, tube 32 is inserted in the end of lead 30 and distal crimp fitting 34 is slid over end of lead 30, aligned with distal crimp, tube 32, and crimped in place. In the preferred embodiment, a length of 0.056 in. ID×0.066 in. OD insulating robing 36 is optionally slid over lead 30 so that it butts against distal crimp, fitting 34.

The braided carbon fiber/conductive metallic wire conductor 22 is cut to an appropriate predetermined length and slid over optional tubing 36 so that the distal end of braided conductor 22 is disposed over part of distal crimp fitting 34 and butts against shoulder 38 of distal crimp fitting 34. Distal compression ring 40 is aligned with distal crimp fitting 34 and the distal end of braided conductor 22 and swaged in place to secure the distal end of braided conductor 22.

Referring to FIG. 4 the proximal end 24 is assembled as follows. The proximal compression ring 42 is slid over the proximal end of braided conductor 22, approximately beyond its final terminal point. Proximal crimp fitting 44 is slid over lead 30 and under the proximal end of braided conductor 22 so that the end of braided conductor 22 butts against shoulder 46 of proximal crimp fitting 44. Proximal crimp fitting 44 is crimped to lead 30. Proximal compression ring 42 is slid back into position over the proximal end of braided conductor 22 and proximal crimp fitting 44 and swaged in place. Insulating tubing 80, preferably 0.056 in. ID×0.076 in. OD, is slid over lead 30 and butted against proximal crimp fitting 44. Insulative robing 48, preferably silicone rubber, preferably 0.058 in. ID×0.077 in. OD, is applied to cover the end of tubing 80, compression fitting 42, and the end of braided conductor 22, then bonded in place with an adhesive such as silicone.

Referring to FIG. 3A, a pace/sense electrode 50 is mounted at the distal end of the implantable assembly 10. The composite electrode assembly 12 is tubular, allowing for internal passage of the coil lead 52 connected to the pace/sense electrode 50. In the preferred embodiment, lead 52 is Trifiler MP35N, 0.021 in. ID×0.034 in OD. Electrode 50 is attached to the end of lead 52 by inserting a piece of 0.010 dia. stainless steel wire 54 inside lead 52 as electrode 50 is pushed onto lead 52. The piece of wire 54 expands lead 52 holding it firm against the bore 56 of electrode 50. Insulating tubing 58, preferably 0.024 in ID×0.032 in. OD, is placed over lead 52 so that it butts against electrode 50, then insulative tubing 60, preferably silicone rubber, preferably 0.058 in. ID×0.077 in. OD, is applied over the joint between tubing 58 and electrode 50 and bonded in place with an adhesive 62, such as silicone. Collar 64 is bonded to electrode 50 with adhesive 62. Collar 64 facilitates tissue growth around it to help anchor the pace/sense electrode assembly 16 in the heart muscle.

Lead 52 with tubing 58 and electrode assembly 16 attached is inserted into distal crimp tube 32 of the composite electrode assembly 12 and pushed down the length of the lead 30. The insulating tubing 58 electrically insulates the two coils. When insulative tubing 60 butts against crimp tube 32, another piece of insulative tubing 66 is installed over distal crimp fitting 34 and distal compression ring 40, so it overlaps insulative tubing 60 and it is bonded in place with adhesive such as silicone.

An alternate embodiment of the pace/sense electrode assembly 16 is shown in FIG. 3B. Pace/sense electrode 70 is modified by boring hole 72 all the way through it and shortening the length from shoulder 74. This makes it easier to install wire 76 because it can be installed from the outside end, then hole 72 sealed with an adhesive 78 such as silicone. The rest of the assembly is as shown in FIG. 3A and described above.

Composite electrode conductor 22 is made in the preferred embodiments by braiding twenty-four tows of carbon fiber, preferably Toray T-300 1K and eight strands of conductive metallic wire, preferably 90/10 platinum iridium 9/49 style over a solid plastic core of 0.063 in. diameter.

Figure 5:
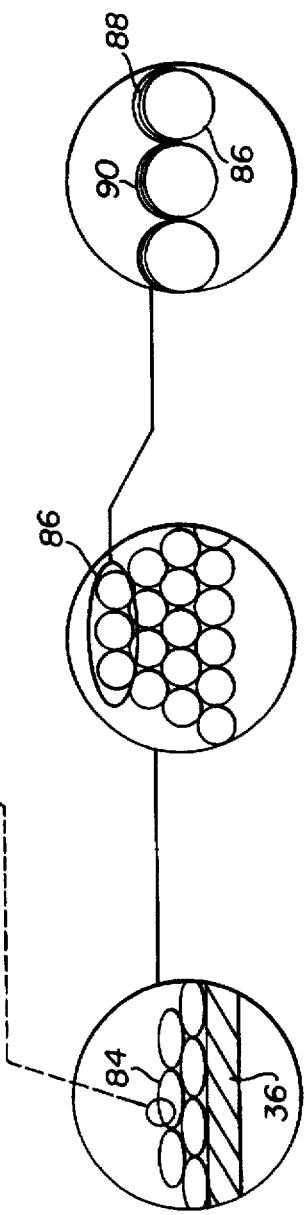
FIG. 5 is an illustration of and alternate embodiment of the fiber conductor of the present invention using titanium and silver coatings on the carbon fiber electrode.

In an alternate embodiment of conductor 22, thirty-two tows of carbon fiber are braided and no conductive metallic wire. In that embodiment, the outside of conductor 22 is coated with a layer of tungsten followed by a layer of silver. Referring to FIG. 5, tows 84 of carbon fiber are intertwined by the braiding process. Each tow has 1000 filaments 86. The titanium 88 and silver 90 coatings are applied only to the outer filaments 86 exposed of the outer tows 84 exposed by the braiding process. Coatings 88 and 90 are applied by vacuum deposition. The total coating thickness on the carbon filaments 86 is approximately 2 microns.

Figure 6:
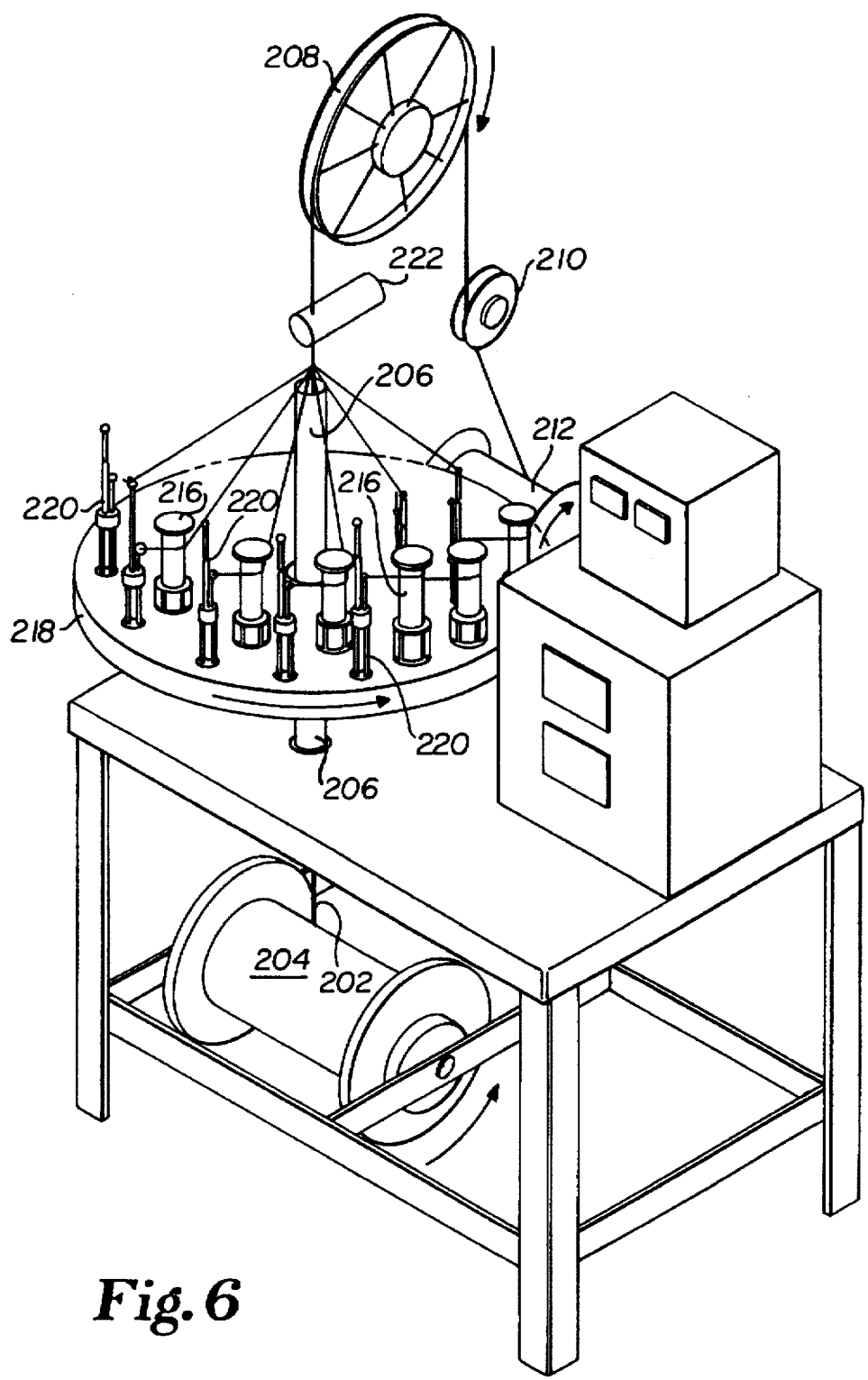
FIG. 6 is an illustration of a braiding machine used to make the fiber conductor of the present invention.

Braiding is done in a continuous operation as illustrated in FIG. 6. Braiding machines are well known in industry, so the description here is only illustrative. Core material 202 is unwound from a supply spool 204 and fed up through tube 206, around wheels 208 and 210, and onto take-up spool 212. Fiber 214 from spools 216 mounted on table 218 is fed through carriers 220 and through guide 222. As wheel 208 advances, carriers 220 move in a serpentine path to braid fiber 214 over core 202. Controlling the speed of the carriers 220 relative to that of wheel 208 controls the braid pattern. The length of the braid is limited only by the length of core 202 on spool 204 and the lengths of fiber 214 on their spools 216.

There are many configurations for the leads connecting to conventional defibrillator and pace/sense electrodes. There are also other structures which can go inside a tubular defibrillation electrode such as drug dispensers and fiber optics. To accommodate leads of any configuration, and any additional structures inside the electrode, an alternate embodiment of the invention is as follows.

Referring to FIG. 7, on distal end 120, lead 130, distal crimp tube 132, distal crimp fitting 134, insulating tubing 136, braided conductor 122, and distal compression ring 140 are assembled as shown and described in the preferred embodiment of FIGS. 3A and 4. Insulative tubing 166 can be installed at this time or after the desired electrode or other structure is installed. At the proximal end 124, lead 130 is cut to a predetermined length to accommodate fittings at this end of the electrode. A proximal crimp tube 143 is inserted inside the proximal end of lead 130. Proximal compression ring 142 and proximal crimp fitting 144 are installed as shown and described in the preferred embodiment of FIGS. 3A and 4. Insulative tubing 148 is installed and bonded with silicone rubber adhesive for example. Proximal crimp fitting 144 has a connector end 146 that can be configured to one of several different mating connector designs per customer requirements. This assembly is hollow to accommodate a plurality of additional conductors or other structures passing through it.

The invention as shown in these embodiments provides a compact package of a most efficient defibrillator electrode specifically designed to be used with at least one additional device. One embodiment shows how the defibrillator electrode of the present invention is used with a pace/sense electrode. The defibrillator electrode provides a comparatively high voltage shock to a fibrillating heart to restore normal rhythm. The pace/sense electrode senses the natural electrical signal produced by a beating heart and/or provides a low voltage stimulation to maintain a desired pace of the heartbeat. The increased efficiency of the defibrillator electrode allows current battery packs to last longer or the same useful life to be obtained from smaller battery packs. It also allows the defibrillator electrode to be much smaller than conventional defibrillator electrodes. A device as shown in these embodiments can easily be placed in the desired location to provide part of the electrical stimulation and sensing needed to control a malfunctioning heart. At least one other electrode is needed to complete the defibrillation circuit. That could be provided by another device of this configuration attached at a different location, or by some other electrode configuration.

The descriptions above and the accompanying drawings should be interpreted in the illustrative and not the limited sense. While the invention has been disclosed in connection with the preferred embodiment or embodiments thereof; it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof; including both structural equivalents and equivalent structures.

The invention claimed is:

1. An implantable biomedical assembly for use in a living body, comprising:
   (a) an electrode for providing a low polarization, low capacitance and low impedance electrical interface with body tissue, wherein said electrode is tubular with a distal end and a proximal end, is flexible, and is comprised of a multiplicity of uninsulated current conducting fibers, said multiplicity of fibers being interlaced, and wherein said multiplicity of fibers provide an effective surface area for said electrical interface which is larger than the apparent surface area of said electrode as determined from linear dimensions of said electrode;
   (b) a tubular conductive lead, said conductive lead being substantially the same length as said electrode and having a distal end and a proximal end;
   (c) connection means which mechanically and electrically connects said conductive lead to said electrode;
   (d) a distal fitting which is mechanically and electrically connected to the distal end of said conductive lead, and where said connection means mechanically and electrically connects said distal end of said electrode to said distal fitting; and
   (e) a proximal fitting, which is configured to connect to an additional structure, where said proximal fitting is mechanically and electrically connected to the proximal end of said conductive lead, and where said connection means mechanically and electrically connects said proximal end of said electrode to said proximal fitting.

2. An implantable assembly of claim 1 where said connection means is applied at said distal end and at said proximal end of said electrode.

3. An implantable assembly of claim 2 where said connection means comprises a compression fitting.

4. An implantable assembly of claim 3 where said compression fitting is comprised of a malleable, conductive material.

5. An implantable assembly of claim 4 where said malleable conductive material is comprised of platinum.

6. An implantable assembly of claim 4 where said malleable conductive material is comprised of platinum-iridium.

7. An implantable assembly of claim 2 where said conductive lead is substantially longer than said electrode, said conductive lead has a first end and a second end, and said electrode is disposed on said first end of said conductive lead.

8. An implantable assembly of claim 7 where said electrode and said conductive lead are tubular, and further comprising:

(a) at least one other electrode mounted distally with respect to said first electrode; and (b) at least one other conductive lead, having a first end and a second end, said first end being conductively connected to said at least one other electrode, and where said at least one other conductive lead runs inside of said first conductive lead for a substantial length of said first conductive lead.

9. An implantable assembly of claim 1 where said connection means comprises a compression fitting.

10. An implantable assembly of claim 9 where said compression fitting is comprised of a malleable, conductive metal.

11. An implantable assembly of claim 10 where said malleable conductive metal is comprised of platinum.

12. An implantable assembly of claim 10 where said malleable conductive metal is comprised of platinum-iridium.

13. An implantable assembly of claim 1 where said fibers are carbon fiber and conductive metallic wire.

14. An implantable assembly of claim 13 where said metallic wire is platinum-iridium.

15. An implantable assembly of claim 14 where the ratio of said carbon fiber to said platinum-iridium wire is 4 tows of 1000-filaments/tow carbon fiber to 1 strand of 9-filament 85 μm diameter wire.

16. An implantable assembly of claim 1 where the outside of said electrode is coated with a thin layer of titanium followed by a thin layer of silver.

17. An implantable biomedical assembly for use in a living body, comprising:

(a) an electrode for providing a low polarization, low capacitance and low impedance electrical interface with body tissue, wherein said electrode has a distal end and a proximal end, is flexible, and is comprised of a multiplicity of uninsulated current conducting carbon fiber and conductive metallic wire fibers, said multiplicity of fibers being interlaced, and wherein said multiplicity of fibers provide an effective surface area for said electrical interface which is larger than the apparent surface area of said electrode as determined from linear dimensions of said electrode, said electrode further having an outside which is coated with a thin layer of titanium followed by a thin layer of silver;

(b) a conductive lead; and (c) connection means which mechanically and electrically connects said conductive lead to said electrode.

18. An implantable biomedical assembly for use in a living body, comprising:

(a) an electrode for providing a low polarization, low capacitance and low impedance electrical interface with body tissue, wherein said electrode has a distal end and a proximal end, is flexible, and is comprised of a multiplicity of uninsulated current conducting fibers, said multiplicity of fibers being interlaced, and wherein said multiplicity of fibers provide an effective surface area for said electrical interface which is larger than the apparent surface area of said electrode as determined from linear dimensions of said electrode wherein the outside of said electrode is coated with a thin layer of titanium followed by a thin layer of silver;

(b) a conductive lead; and (c) connection means which mechanically and electrically connects said conductive lead to said electrode.

* * * * *